United States Patent
Lee et al.

(10) Patent No.: US 12,311,005 B2
(45) Date of Patent: May 27, 2025

(54) PHARMACEUTICAL COMPOSITIONS AND USES THEREOF IN TREATING PARKINSON'S DISEASE

(71) Applicant: Tzung-Yan Lee, New Taipei (TW)

(72) Inventors: Tzung-Yan Lee, New Taipei (TW); Hen-Hong Chang, Taichung (TW); Yann-Lii Leu, New Taipei (TW); Hsuan-Miao Liu, Hsinchu (TW); Wei-Han Chiang, Taipei (TW); Jheng-Huei Wang, Taoyuan (TW)

(73) Assignee: Tzung-Yan Lee, New Taipei (TW)

( * ) Notice: Subject to any disclaimer, the term of this patent is extended or adjusted under 35 U.S.C. 154(b) by 337 days.

(21) Appl. No.: 17/921,141

(22) PCT Filed: Sep. 11, 2020

(86) PCT No.: PCT/CN2020/114665
§ 371 (c)(1),
(2) Date: Oct. 25, 2022

(87) PCT Pub. No.: WO2022/052016
PCT Pub. Date: Mar. 17, 2022

(65) Prior Publication Data
US 2023/0190845 A1    Jun. 22, 2023

(51) Int. Cl.
| | | |
|---|---|---|
| *A61K 36/282* | (2006.01) | |
| *A61K 31/12* | (2006.01) | |
| *A61K 31/216* | (2006.01) | |
| *A61K 31/24* | (2006.01) | |
| *A61K 31/352* | (2006.01) | |
| *A61K 31/704* | (2006.01) | |
| *A61K 31/7048* | (2006.01) | |
| *A61K 36/484* | (2006.01) | |
| *A61K 36/533* | (2006.01) | |
| *A61K 36/605* | (2006.01) | |
| *A61K 36/81* | (2006.01) | |
| *A61K 36/899* | (2006.01) | |
| *A61K 36/9066* | (2006.01) | |

(52) U.S. Cl.
CPC .......... *A61K 36/282* (2013.01); *A61K 31/12* (2013.01); *A61K 31/216* (2013.01); *A61K 31/24* (2013.01); *A61K 31/352* (2013.01); *A61K 31/704* (2013.01); *A61K 31/7048* (2013.01); *A61K 36/484* (2013.01); *A61K 36/533* (2013.01); *A61K 36/605* (2013.01); *A61K 36/81* (2013.01); *A61K 36/899* (2013.01); *A61K 36/9066* (2013.01); *A61K 2236/333* (2013.01)

(58) Field of Classification Search
CPC .... A61K 36/282; A61K 31/12; A61K 31/216; A61K 31/24; A61K 31/352; A61K 31/704; A61K 31/7048; A61K 36/484; A61K 36/533; A61K 36/605; A61K 36/81; A61K 36/899; A61K 36/9066; A61K 2236/333
See application file for complete search history.

(56) References Cited

FOREIGN PATENT DOCUMENTS

| | | | | |
|---|---|---|---|---|
| CN | 107349213 | * | 11/2017 | |
| CN | 107349213 A | * | 11/2017 | |
| CN | 109200054 | * | 1/2019 | |
| CN | 109200054 A | * | 1/2019 | |
| CN | 109674777 | * | 4/2019 | |
| CN | 109674777 A | * | 4/2019 | |
| WO | WO 2009121155 | * | 10/2009 | |
| WO | WO-2009121155 A2 | * | 10/2009 | ........... A61K 31/352 |

OTHER PUBLICATIONS

Enogieru et al, Oxid Med Cell Longev (2018).*

* cited by examiner

Primary Examiner — Shirley V Gembeh
(74) Attorney, Agent, or Firm — NZ Carr Law Office

(57) ABSTRACT

Disclosed herein are pharmaceutical compositions and uses thereof in treating Parkinson's disease. The pharmaceutical composition comprises an ethanol extract of an herbal mixture consisting of *Artemisia argyi*, *Morus alba* L., *Leonurus japonicus* Houtt, *Capsicum annuum* L., *Lophatherum gracile* Brongn, *Curcuma longa*, and *Glycyrrhiza uralensis*; and a pharmaceutically acceptable excipient. The ethanol extract comprise 14 ingredients, including chlorogenic acid, leonurine, schaftoside, rutin, isochaftoside, isochlorogenic acid, 4,5-dicaffeoylquinic acid, quercetin, apigenin, glycyrrhizic acid, bisdemethoxycurcumin, demethoxycurcumin, curcumin and artemisetin.

7 Claims, 7 Drawing Sheets

PHARMACEUTICAL COMPOSITIONS AND USES THEREOF IN TREATING PARKINSON'S DISEASE

This application is a U.S. National Stage Filing under 35 U.S.C. 371 from International Patent Application Serial No. PCT/CN2020/114665, filed Sep. 11, 2020, and published on Mar. 17, 2022, the disclosure of which is incorporated by reference herein in its entirety.

BACKGROUND OF THE INVENTION

1. Field of the Invention

The present disclosure in general relates to the field of disease treatment. More particularly, the present disclosure relates to novel pharmaceutical compositions, and their uses in the treatment of Parkinson's disease (PD).

2. Description of Related Art

Parkinson's disease (PD) is a neurodegenerative disorder that affects the movement of patients. The symptoms of PD usually begin gradually, and get worse over time. The most obvious symptoms in the early stage of PD include shaking, rigidity, and slowness of movement (bradykinesia). As the disorder progresses, patients may have difficulty in walking and talking. Mental and behavioral changes (such as impaired posture and balance, loss of automatic movement, speech changes, and writing changes), sleep problems, depression, anxiety, memory difficulties (e.g., dementia), and fatigue are also reported in some patients. PD typically occurs in people over the age of 60, while about 5 to 10% of PD patients have a "early-onset" disorder, which begins before the age of 50. The average life expectancy following diagnosis is about 7 to 15 years. Although some cases of PD appear to be hereditary, and a few can be traced to specific genetic mutations, in most cases the disorder occurs randomly and does not seem to run in families. Many researchers believe that PD results from a combination of genetic factors and environmental factors such as exposure to toxins.

Up to the present day, there is no cure for PD. Some medicines (including levodopa, dopamine agonists, and monoamine oxidase B (MAO-B) inhibitors), surgery, and physical treatment are reported to relieve the symptoms of PD; unfortunately, none of these treatments provides a satisfactory result due to the limitations of side effects, drug tolerance, the development of complications, and/or low efficacy. In view of the foregoing, there remains a continue interest in identifying new methods and/or agents for treating PD.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, the present disclosure is directed to novel pharmaceutical compositions, and their uses in the treatment of PD.

The first aspect of the present disclosure is directed to a pharmaceutical composition comprising an ethanol extract of an herbal mixture consisting of *Artemisia argyi*, *Morus alba* L., *Leonurus japonicus* Houtt, *Capsicum annuum* L., *Lophatherum gracile* Brongn, *Curcuma longa*, and *Glycyrrhiza uralensis*; and a pharmaceutically acceptable excipient.

According to certain embodiments of the present disclosure, the ethanol extract is obtained via extracting *Artemisia argyi*, *Morus alba* L., *Leonurus japonicus* Houtt, *Capsicum annuum* L., *Lophatherum gracile* Brongn, *Curcuma longa*, and *Glycyrrhiza uralensis* by ethanol at about 30-100° C. for about 0.5-5 hours.

According to some preferred embodiments, the ethanol extract is obtained via extracting the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis* by 95% ethanol at about 50-80° C. for about 3-5 hours.

In some embodiments, during the extraction, the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis* are mixed at a weight ratio of about 4-6:4-6:4-6:2-3:2-3:1:1. According to specific examples, the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis* are mixed at a weight ratio of about 5:5:5:2.5:2.5:1:1.

According to certain embodiments, the thus-obtained ethanol extract comprises 14 herbal ingredients, including chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, and artemisetin. According to some working examples, the herbal ingredient containing ethanol extract provides a potential means to treat PD via regulating different molecules in PD pathogenic pathway and/or improving mitochondrial function.

The second aspect of the present disclosure thus pertains to a pharmaceutical composition comprising a mixture of chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, and artemisetin; and a pharmaceutically acceptable excipient.

According to some embodiments of the present disclosure, the mixture comprises 5-10 wt % of chlorogenic acid, 0.1-2 wt % of leonurine, 0.1-2 wt % of schaftoside, 5-10 wt % of rutin, 35-45 wt % of isoschaftoside, 20-30 wt % of isochlorogenic acid, 3-6 wt % of 4,5-dicaffeoylquinic acid, 0.1-0.5 wt % of quercetin, 1-3 wt % of apigenin, 1-3 wt % of glycyrrhizic acid, 1-3 wt % of bisdemethoxycurcumin, 1-3 wt % of demethoxycurcumin, 5-10 wt % of curcumin, and 0.1-0.5 wt % of artemisetin.

In certain preferred embodiments, the mixture comprises 7-8 wt % of chlorogenic acid, 0.5-1 wt % of leonurine, 0.5-1.5 wt % of schaftoside, 7-8 wt % of rutin, 38-42 wt % of isoschaftoside, 20-25 wt % of isochlorogenic acid, 4-5 wt % of 4,5-dicaffeoylquinic acid, 0.1-0.3 wt % of quercetin, 1-2 wt % of apigenin, 1-2 wt % of glycyrrhizic acid, 2-3 wt % of bisdemethoxycurcumin, 2-3 wt % of demethoxycurcumin, 5-7 wt % of curcumin, and 0.1-0.3 wt % of artemisetin.

Also disclosed herein is a method of treating PD in a subject by use of the present pharmaceutical composition. The method comprises administering to the subject an effective amount of the pharmaceutical composition in accordance with any aspect or embodiment of the present disclosure.

According to some embodiments of the present disclosure, the pharmaceutical composition is orally administered to the subject. In preferred embodiments, the pharmaceutical composition is administered to the subject daily for at least 7 days; more preferably, at least 14 days. In one specific example, the pharmaceutical composition is administered to the subject daily for 14 days.

The subject treatable with the present pharmaceutical composition and/or method is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

Figure 1:
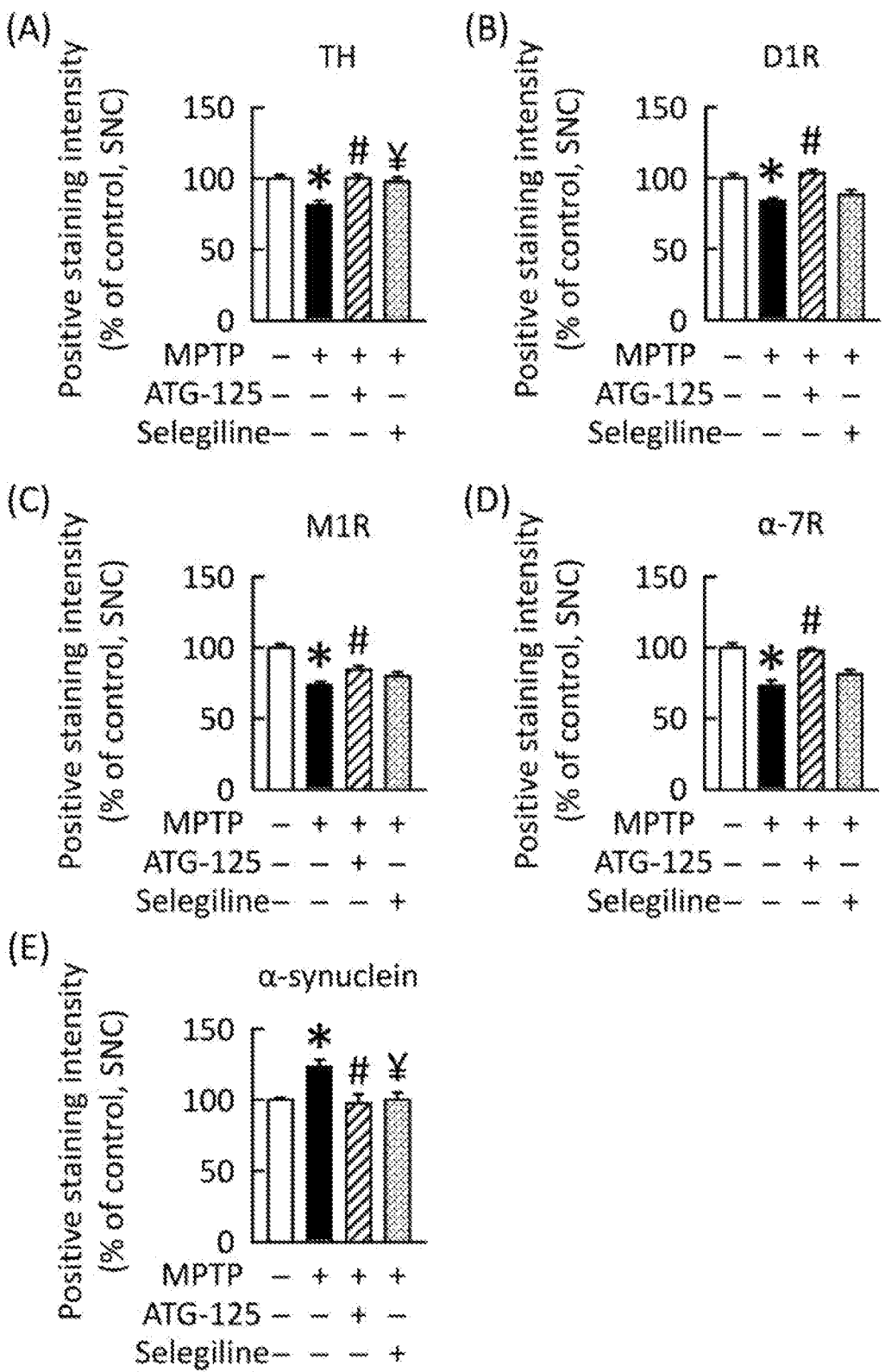
FIG. 1 depicts the effect of the present ATG-125 on the expression levels of tyrosine hydroxylase (TH; Panel (A)), type 1 dopamine receptor (D1R; Panel (B)), type 1 muscarinic receptor (MIR; Panel (C)), alpha-7 nicotinic receptor (α-7R; Panel (D)), and α-synuclein (Panel (E)) in the substantia nigra (SNC) of mice administered with specified treatments according to Example 1 of the present disclosure; for each animal group, n=5; *P<0.05, the normal control group compared to the MPTP group; #P<0.05, the MPTP group compared to the MPTP+ATG-125 group; YP<0.05, the MPTP group compared to the MPTP+selegiline group.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about"

means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "extract" encompasses crude extracts as well as processed or refined extract. Specifically, crude extracts are prepared by a simple extraction in which selected plant ingredients are bought into contact with at least one extractant (i.e., extracting solvent). In some optional cases, the thus-obtained crude extracts are subjected to one or more separation and/or purification steps to obtain purified, processed or refined extracts. The plant extract may be in liquid form, such as a solution, concentrate, or distillate; or it may be in solid form in which the solvent is removed, such as in paste, granulate or powder form.

The term "weight percentage" (wt %) as used herein refers to the weight percentage of an ingredient (e.g., the chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, or artemisetin of the present pharmaceutical composition) in a mixture containing the ingredient. The weight percentage (wt %) is calculated as the weight of the ingredient divided by the total weight of the mixture expressed in percentage and/or decimal.

As used herein, the term "weight ratio" refers to the amounts of each component (e.g., the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis*) in a mixture (e.g., the herbal mixture of the present disclosure) as a ratio of the weight of each component.

As used herein, the term "treat," "treating" and "treatment" are interchangeable, and encompasses partially or completely preventing, ameliorating, mitigating and/or managing a symptom, a secondary disorder or a condition associated with PD. The term "treating" as used herein refers to application or administration of the pharmaceutical composition of the present disclosure to a subject, who has a symptom, a secondary disorder or a condition associated with PD, with the purpose to partially or completely prevent, alleviate, ameliorate, relieve, delay onset of, inhibit progression of, reduce severity of, and/or reduce incidence of one or more symptoms, secondary disorders or features associated with PD. Symptoms, secondary disorders, and/or conditions associated with PD include, but are not limited to, shaking, rigidity, slowness of movement (bradykinesia), difficulty in walking and talking, impaired posture and balance, loss of automatic movement, speech changes, writing changes, sleep problems, depression, anxiety, memory difficulties (e.g., dementia) and fatigue. Treatment may be administered to a subject who exhibits only early signs of such symptoms, disorder, and/or condition for the purpose of decreasing the risk of developing the symptoms, secondary disorders, and/or conditions associated with PD. Treatment is generally "effective" if one or more symptoms or clinical markers are reduced as that term is defined herein. Alternatively, a treatment is "effective" if the progression of a symptom, disorder or condition is reduced or halted.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the mixture of specified compounds, or the ethanol extract of the herbal mixture of the present pharmaceutical composition), such as molar concentration, mass concentration, volume concentration, molality, mole fraction, mass fraction and mixing ratio. Persons having ordinary skills could calculate the human equivalent dose (HED) for the medicament (such as the pharmaceutical composition of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The terms "subject" and "patient" are used interchangeably herein, and are intended to mean an animal including the human species that is treatable by the pharmaceutical composition and/or method of the present invention. The term "subject" or "patient" intended to refer to both the male and female gender unless one gender is specifically indicated. Accordingly, the term "subject" or "patient" comprises any mammal, which may benefit from the pharmaceutical composition or the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the subject is a human.

II. Description of The Invention (i) Pharmaceutical Compositions

The subject invention aims at providing methods of treating PD in a subject, as well as the pharmaceutical preparations or the dietary supplements for use in practicing the subject methods.

Accordingly, the first aspect of the present disclosure pertains to a pharmaceutical composition, which provides a potential means to treat a subject having or suspected of having PD. The pharmaceutical composition comprises an extract of an herbal mixture consisting of *Artemisia argyi* (commonly known as "silvery wormwood" or "Chinese mugwort"), *Morus alba* L. (also known as "white mulberry"), *Leonurus japonicus* Houtt (also known as "Chinese motherwort"), *Capsicum annuum* L. (commonly known as "chili" or "pepper"), *Lophatherum gracile* Brongn, *Curcuma longa* (commonly known as "turmeric"), and *Glycyrrhiza uralensis* (also known as "Chinese liquorice"); and a pharmaceutically acceptable excipient.

According to some embodiments, *Artemisia argyi*, *Morus alba* L., *Leonurus japonicus* Houtt, *Capsicum annuum* L., *Lophatherum gracile* Brongn, *Curcuma longa*, and *Glycyrrhiza uralensis* are mixed and extracted by a solvent (e.g., water or ethanol) at suitable temperature for a period of time so as to obtain the present extract, which contains active ingredients, i.e., ingredients providing therapeutically beneficial effects on PD.

Depending on desired purposes, the solvent for extracting said herbs (i.e., a combination of *Artemisia argyi*, *Morus alba* L., *Leonurus japonicus* Houtt, *Capsicum annuum* L., *Lophatherum gracile* Brongn, *Curcuma longa*, and *Glycyrrhiza uralensis*) may be a supercritical fluid (SFC; such as carbon dioxide, water, methane, ethane, propane, ethene, propene, methanol, ethanol, and acetone), water, $C_{1-4}$ alcohol (such as ethanol, 1-propanol, n-butanol, iso-butanol, and ter-butanol), acetone, ethyl acetate, n-hexane, or a combination thereof. According to some embodiments, said herbs are extracted by 75-100% (such as 75, 76, 77, 78, 79, 80, 81, 82, 83, 84, 85, 86, 87, 88, 89, 90, 91, 92, 93, 94, 95, 96, 97, 98, 99, or 100%) ethanol at a temperature of about 30-100° C. (such as 30, 35, 40, 45, 50, 55, 60, 65, 70, 75, 80, 85, 90, 95, or 100° C.) for a period of about 0.5-5 hours (such as 0.5, 0.6, 0.7, 0.8, 0.9, 1, 1.5, 2, 2.5, 3, 3.5, 4, 4.5, or 5 hours) thereby obtaining the extract of the present pharmaceutical composition.

According to certain examples, the extract of the present pharmaceutical composition is prepared via mixing the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis*, and extracting the mixed herbal parts or the herbal mixture by 95% ethanol at about 50-80° C. for about 3-5 hours. In one exemplary embodiment, the extract of the present pharmaceutical composition is prepared by extracting said herbal mixture or herbal parts (i.e., the leaves of *Artemisia argyi*, the leaves of *Morus alba* L., the leaves of *Leonurus japonicus* Houtt, the leaves of *Capsicum annuum* L., the leaves of *Lophatherum gracile* Brongn, the roots of *Curcuma longa*, and the roots of *Glycyrrhiza uralensis*) by 95% ethanol at about 70° C. for about 4 hours.

According to certain embodiments of the present disclosure, said herbal parts are mixed at a weight ratio of about 4-6 (e.g., 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6):4-6 (e.g., 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6):4-6 (e.g., 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6):2-3 (e.g., 2, 2.1, 2.2, 2.3, 2.4, 2.5, 2.6, 2.7, 2.8, 2.9, or 3):2-3 (e.g., 2, 2.1, 2.2, 2.3, 2.4, 2.5, 2.6, 2.7, 2.8, 2.9, or 3):1:1. As could be appreciated, the person having ordinary skill in the art may adjust the ratio of said herbal parts in accordance with intended purposes. For example, said herbal parts may be mixed at a weight ratio of about 4:4:4:2:2:1:1. Alternatively, said herbal parts may be mixed at a weight ratio of about 4.5:5:6:2.5:2:1:1. Still alternatively, said herbal parts may be mixed at a weight ratio of about 5:5:5:2:3:1:1. According to some working examples of the present disclosure, said herbal parts are mixed at a weight ratio of about 5:5:5:2.5:2.5:1:1, and extracted by the solvent to produce a crude extract. The crude extract may subsequently be filtered, concentrated and/or lyophilized (i.e., freeze-dried) to produce a crude extract powder or paste. Alternatively, it may be subject to further purification, such as column chromatography or precipitation, to produce a refined extract.

According to some embodiments, the thus-obtained extract contains active ingredients useful in treating PD; the active ingredients include, at least, chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, and artemisetin.

Thus, the second aspect of the present disclosure provides a pharmaceutical composition comprising a mixture of compounds, and a pharmaceutically acceptable excipient, in which the mixture consists of 14 active ingredients, including, (1) chlorogenic acid, which has a structure of

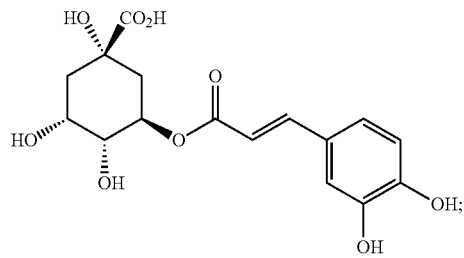 [SMILES: O=C(/C=C/c1ccc(O)c(O)c1)O[C@@H]1C[C@](O)(C(=O)O)C[C@@H](O)[C@H]1O]

(2) leonurine, which has a structure of

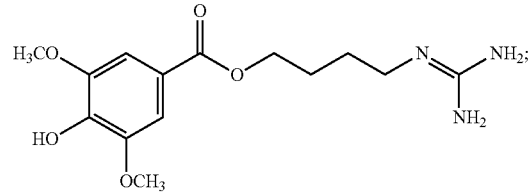 [SMILES: COc1cc(C(=O)OCCCCN=C(N)N)cc(OC)c1O]

(3) schaftoside, which has a structure of

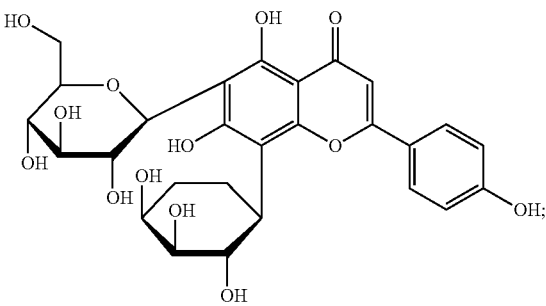

(4) rutin, which has a structure of

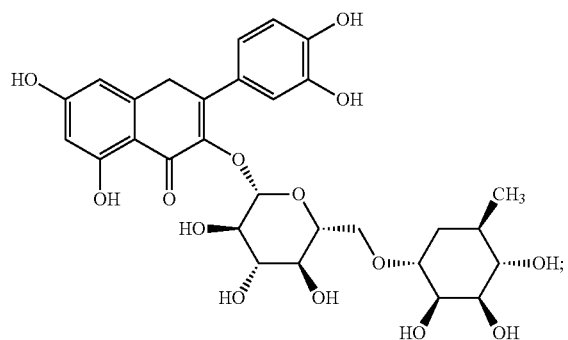 [SMILES: C[C@@H]1C[C@@H](OC[C@H]2O[C@@H](OC3=C(c4ccc(O)c(O)c4)Cc4cc(O)cc(O)c4C3=O)[C@H](O)[C@@H](O)[C@@H]2O)[C@H](O)[C@H](O)[C@H]1O]

(5) isoschaftoside, which has a structure of

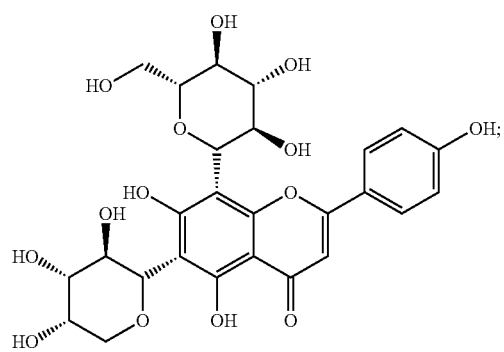

(6) isochlorogenic acid, which has a structure of

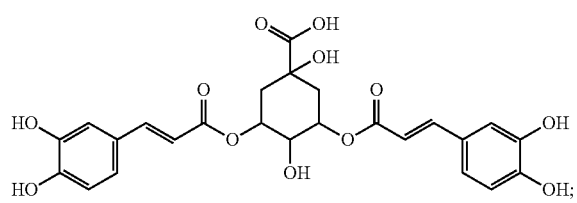 [SMILES: O=C(/C=C/c1ccc(O)c(O)c1)OC1CC(O)(C(=O)O)CC(OC(=O)/C=C/c2ccc(O)c(O)c2)C1O]

(7) 4,5-dicaffeoylquinic acid, which has a structure of

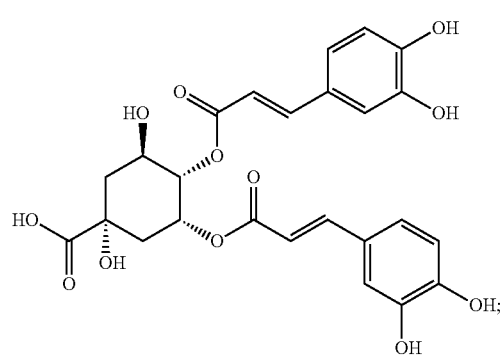 [SMILES: O=C(/C=C/c1ccc(O)c(O)c1)O[C@H]1[C@H](O)C[C@](O)(C(=O)O)C[C@H]1OC(=O)/C=C/c1ccc(O)c(O)c1]

(8) quercetin, which has a structure of

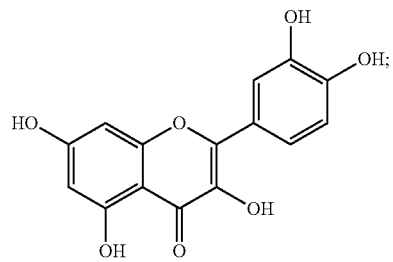 [SMILES: O=c1c(O)c(-c2ccc(O)c(O)c2)oc2cc(O)cc(O)c12]

(9) apigenin, which has a structure of

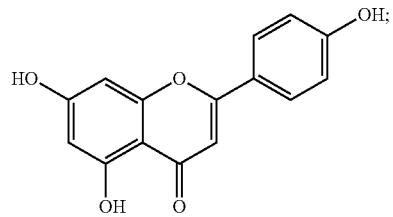 [SMILES: O=c1cc(-c2ccc(O)cc2)oc2cc(O)cc(O)c12]

(10) glycyrrhizic acid, which has a structure of

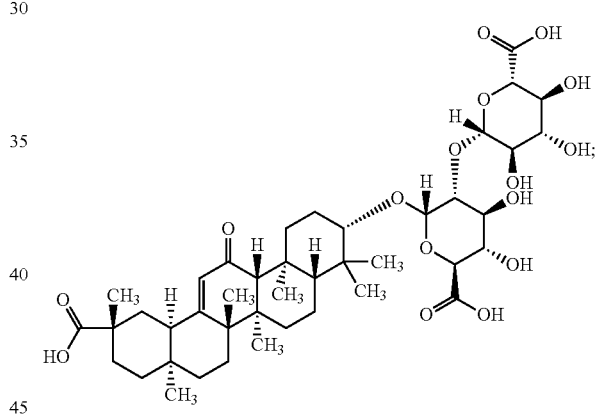

(11) bisdemethoxycurcumin, which has a structure of

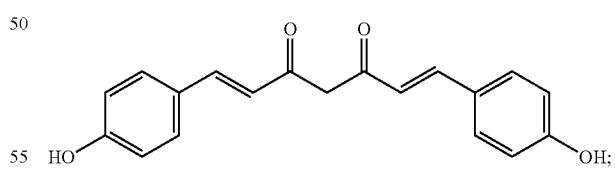

(12) demethoxycurcumin, which has a structure of

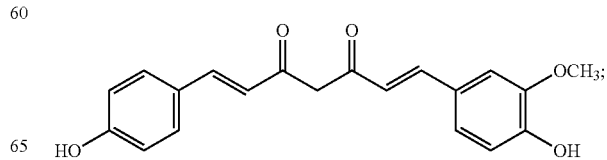

(13) curcumin, which has a structure of

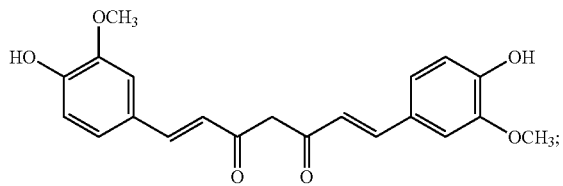 [SMILES: COc1cc(/C=C/C(=O)CC(=O)/C=C/c2ccc(O)c(OC)c2)ccc1O]

and
(14) artemisetin, which has a structure of

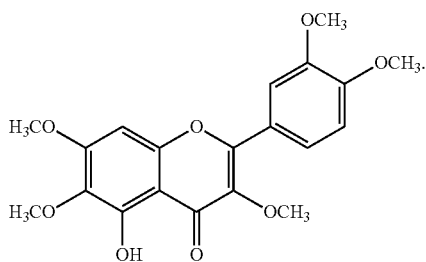 [SMILES: COc1ccc(-c2oc3cc(OC)c(OC)c(O)c3c(=O)c2OC)cc1OC]

According to some embodiments,
(1) chlorogenic acid is present in the mixture at a level of about 5-10% (e.g., 5, 5.5, 6, 6.5, 7, 7.5, 8, 8.5, 9, 9.5, or 10%) by weight (i.e., 5-10 wt %), based on the total weight of the mixture;
(2) leonurine is present in the mixture at a level of about 0.1-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2%) by weight (i.e., 0.1-2 wt %) based on the total weight of the mixture;
(3) schaftoside is present in the mixture at a level of about 0.1-2% (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2%) by weight (i.e., 0.1-2 wt %) based on the total weight of the mixture;
(4) rutin is present in the mixture at a level of about 5-10% (e.g., 5, 5.5, 6, 6.5, 7, 7.5, 8, 8.5, 9, 9.5, or 10%) by weight (i.e., 5-10 wt %), based on the total weight of the mixture;
(5) isoschaftoside is present in the mixture at a level of about 35-45% (e.g., 35, 35.5, 36, 36.5, 37, 37.5, 38, 38.5, 39, 39.5, 40, 40.5, 41, 41.5, 42, 42.5, 43, 43.5, 44, 44.5, or 45%) by weight (i.e., 35-45 wt %), based on the total weight of the mixture;
(6) isochlorogenic acid is present in the mixture at a level of about 20-30% (e.g., 20, 20.5, 21, 21.5, 22, 22.5, 23, 23.5, 24, 24.5, 25, 25.5, 26, 26.5, 27, 27.5, 28, 28.5, 29, 29.5, or 30%) by weight (i.e., 20-30 wt %), based on the total weight of the mixture;
(7) 4,5-dicaffeoylquinic acid is present in the mixture at a level of about 3-6% (e.g., 3, 3.5, 4, 4.5, 5, 5.5, or 6%) by weight (i.e., 3-6 wt %), based on the total weight of the mixture;
(8) quercetin is present in the mixture at a level of about 0.1-0.5% (e.g., 0.1, 0.2, 0.3, 0.4, or 0.5%) by weight (i.e., 0.1-0.5 wt %), based on the total weight of the mixture;
(9) each of apigenin, glycyrrhizic acid, bisdemethoxycurcumin and demethoxycurcumin is independently present in the mixture at a level of about 1-3% (e.g., 1, 2, or 3%) by weight (i.e., 1-3 wt %), based on the total weight of the mixture;
(10) curcumin is present in the mixture at a level of about 5-10% (e.g., 5, 5.5, 6, 6.5, 7, 7.5, 8, 8.5, 9, 9.5, or 10%) by weight (i.e., 5-10 wt %), based on the total weight of the mixture; and
(11) artemisetin is present in the mixture at a level of about 0.1-0.5% (e.g., 0.1, 0.2, 0.3, 0.4, or 0.5%) by weight (i.e., 0.1-0.5 wt %), based on the total weight of the mixture.

According to some exemplary embodiments, the mixture comprises 7-8 wt % of chlorogenic acid, 0.5-1 wt % of leonurine, 0.5-1.5 wt % of schaftoside, 7-8 wt % of rutin, 38-42 wt % of isoschaftoside, 20-25 wt % of isochlorogenic acid, 4-5 wt % of 4,5-dicaffeoylquinic acid, 0.1-0.3 wt % of quercetin, 1-2 wt % of apigenin, 1-2 wt % of glycyrrhizic acid, 2-3 wt % of bisdemethoxycurcumin, 2-3 wt % of demethoxycurcumin, 5-7 wt % of curcumin, and 0.1-0.3 wt % of artemisetin.

According to one specific example, the mixture comprises 7.7 wt % of chlorogenic acid, 0.8 wt % of leonurine, 1 wt % of schaftoside, 7.2 wt % of rutin, 40.9 wt % of isoschaftoside, 23.8 wt % of isochlorogenic acid, 4.8 wt % of 4,5-dicaffeoylquinic acid, 0.2 wt % of quercetin, 1.2 wt % of apigenin, 1.8 wt % of glycyrrhizic acid, 2.2 wt % of bisdemethoxycurcumin, 2.2 wt % of demethoxycurcumin, 6 wt % of curcumin, and 0.2 wt % of artemisetin.

The pharmaceutical composition of the present disclosure is preferably freeze dried or lyophilized, and stores in a cool and dry environment until use.

Depending on desired purposes, the pharmaceutical composition according to any aspect, embodiment or example of the present disclosure may be formulated with one or more appropriate pharmaceutically acceptable carriers or excipients, and may be formulated into solid, semi-solid, or liquid dosage forms, such as pills, tablets, capsules, powders, pastes, granules, and ointments. As such, the administration of the active ingredients (e.g., the extract of said herbs or said herbal parts, or the mixture of said compounds) can be achieved in various ways, including oral, buccal, topical, and parenteral etc. administration. In pharmaceutical dosage forms, the pharmaceutical composition of the present disclosure may be administered alone or in combination with other known pharmaceutically active agent to treat PD. One of skilled person in the art is familiar with the various dosage forms that are suitable for use in each route. It is to be noted that the most suitable route in any given case would depend on the nature or severity of the disease or condition being treated.

In some embodiments, the pharmaceutical composition of the present disclosure is formulated into solid dosage forms for oral administration. Such solid dosage forms may be capsules, sachets, tablets, pills, lozengens, powders or granules. In such forms, the active ingredients of the present pharmaceutical composition (including chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, and artemisetin) are optionally mixed with one pharmaceutically acceptable carrier or excipient. Any of the described solid dosage forms may optionally contain coatings and shells, such as enteric coatings, and coatings for modifying the release rate of any of the ingredients. Examples of such coatings are well known in the art. In one example, the pharmaceutical compositions of the present disclosure are tablets such as quick-release tablets. In still another example, the pharmaceutical compositions of the present disclosure are formulated into sustained release forms. In another example, the pharmaceutical compositions of the present disclosure are powders that are encapsulated in soft and hard gelatin capsules.

In some embodiments, the pharmaceutical composition of the present disclosure is formulated into liquid dosage forms for oral administration. The liquid formulation may further include a buffering agent to maintain a desired pH. The liquid dosage formulations may also be filled into soft gelatin capsules. For example, the liquid may include a solution, suspension, emulsion, micro-emulsion, precipitate or any desired liquid media carrying the active ingredients of the present pharmaceutical composition. The liquid may be designed to improve the solubility of the active ingredients of the present pharmaceutical composition to form a drug-containing emulsion or disperse phase upon release. According to one working example of the present disclosure, the active ingredients of the present pharmaceutical composition are formulated with a solvent containing 95% olive oil and 5% glycerol for oral administration.

In some embodiments, the pharmaceutical composition of the present disclosure is formulated into a dosage form for parenteral administration, such as topical administration or injection, which includes, but is not limited to, subcutaneous, intramuscular, intraperitoneal and intravenous injection. The pharmaceutical composition may be formulated as isotonic suspensions, solutions or emulsions in oily or aqueous vehicles, and may contain formulatoary agents such as suspending, stabilizing or dispersing agents. Alternatively, the compositions may be provided in dry form such as powders, crystallines or freeze-dried solids with sterile pyrogen-free water or isotonic saline before use. They may be presented in sterile ampoules or vials.

(ii) Uses of the Present Pharmaceutical Compositions

The second aspect of the present disclosure pertains to a method of treating PD in a subject. The method comprises administering to the subject an effective amount of the pharmaceutical composition in accordance with any aspect, embodiment or example of the present disclosure.

In certain embodiments, the pharmaceutical composition of the present disclosure is given to the subject via oral administration. However, the present disclosure is not limited thereto.

According to embodiments of the present disclosure, the pharmaceutical composition of the present invention is orally administered to the subject in a single dose or in multiple doses (e.g., 2, 3, 4, 5, 6, 7, 8, 9, 10, 11, 12, 13, 14, or more doses).

In one embodiment, the subject is a mouse.

To elicit a therapeutic effect in mice, about 1-1,000 mg/Kg body weight per dose of the present pharmaceutical composition is administered to the subject; preferably, about 10-100 mg/Kg body weight per dose of the present pharmaceutical composition is administered to the subject; more preferably, 50-70 mg of the present pharmaceutical composition per Kg body weight per dose is sufficient to elicit a therapeutic effect on PD in the subject. In one specific example, 60 mg/Kg of the present pharmaceutical composition is administered to the subject thereby achieving the therapeutic effect.

A skilled artisan may readily determine the human equivalent dose (HED) of the present pharmaceutical composition, based on the doses determined from animal studies provided in working examples of this application. Accordingly, the effective amount of the present pharmaceutical composition suitable for use in a human subject may be in the range of 0.1-100 mg/Kg body weight per dose for human; preferably, 1-10 mg/Kg body weight per dose. In one preferred example, the effective HED is about 4-6 mg/Kg body weight per dose.

According to certain preferred embodiments, the pharmaceutical composition of the present disclosure is administered to the subject daily for at least 7 days; for example, being administered to the subject daily for 7, 8, 9, 10, 11, 12, 13, 14, or more day. In one specific example, the pharmaceutical composition of the present disclosure is administered to the subject daily for 14 days.

As could be appreciated, the skilled artisan or clinical practitioner may adjust the dosage or regime in accordance with the physical condition of the patient or the severity of the diseases.

Depending on intended purposes, the present pharmaceutical composition can be applied to the subject, alone or in combination with additional therapies that have some beneficial effects on the prevention or treatment of PD. The present pharmaceutical composition can be applied to the subject before, during, or after the administration of the additional therapies.

The subject treatable by the present pharmaceutical composition and/or method is a mammal, for example, human, mouse, rat, guinea pig, hamster, monkey, swine, dog, cat, horse, sheep, goat, cow, and rabbit. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Preparation of the Present Pharmaceutical Composition (ATG-125)

Seven herbal ingredients, including the leaves of *Artemisia argyi* (512 g), the leaves of mulberry (Moms alba L.; 512 g), the leaves of *Leonurus japonicus* Houtt. (512 g), the leaves of *Capsicum annuum* L. (256 g), the leaves of *Lophatherum gracile* Brongn (256 g), the roots of *Curcuma longa* (103 g), and the roots of *Glycyrrhiza uralensis* (103 g), were soaked in 15 L of 95% ethanol at room temperature for 1 day followed by filtration. The filtrate was retained, and the herbal ingredients were subjected to another soaking treatment in the same manner as previously described. The filtrates were combined, and extracted in 70° C. water-bath for 4 hours followed by filtration. The extraction steps were repeated twice. All separate extractions were mixed and concentrated under reduced pressure. The following yields were obtained: 331.11 g (14.69%).

According to the analytic results of high performance liquid chromatography (HPLC) and liquid chromatography-mass spectrometry (LC/MS), the thus-obtained ethanol extract contained chlorogenic acid (0.38% by weight), leonurine (0.04% by weight), schaftoside (0.05% by weight), rutin (0.36% by weight), isoschaftoside (2.03% by weight), isochlorogenic acid (1.18% by weight), 4,5-dicaffeoylquinic acid (0.24% by weight), quercetin (0.01% by weight), apigenin (0.06% by weight), glycyrrhizic acid (0.09% by weight), bisdemethoxycurcumin (0.11% by weight), demethoxycurcumin (0.11% by weight), curcumin (0.3% by weight), and artemisetin (0.01% by weight), based on the total weight of the ethanol extract (data not shown).

Prior to use in in vivo experiments, 1.5 g of the ethanol extract was soluble in 100 ml solvent consisting of 95% olive oil and 5% glycerol, and the solution was designated as "ATG-125" solution.

Animal Model

C57BL/6 male mice were housed (5 mice/cage, 12 hour light/dark cycle) in a mean constant temperature (25±1.0° C.) with 60-70% relative humidity, and had access to food and water ad libitum. All animal experiments were approved by the Animal Care and Use Committee. After mice adapted for one week, they were randomly divided into 4 groups, including, (1) normal control group, (2) MPTP group, (3) MPTP+ATG-125 group, and (4) MPTP+selegiline group, in which selegiline served as a positive control group in this experiment. To establish the PD model, mice were injected with phosphate buffered saline (PBS; serving as the normal control group) or 1-methyl-4-phenyl-1,2,3,6-tetrahydropyridine (MPTP) (dissolved in PBS, 25 mg/kg, i.p. injection) for 7 consecutive days. After the last MPTP injection, mice were given olive oil (i.e., the MPTP group), ATG-125 solution (60 mg/kg, diluted in olive oil, oral administration; i.e., the MPTP+ATG-125 group), or selegiline (1 mg/kg, diluted in olive oil, i.p. injection; i.e., the MPTP+selegiline group) for 14 consecutive days. 15 days after the last MPTP injection, all animals were sacrificed for further study.

Histology, Immunohistochemistry and Immunofluorescence

Brain tissues of mice were fixed in 4% paraformaldehyde, processed for paraffin embedding and cutting into 5 μm thick sections. Before immunostaining, tissue samples were deparaffinized through xylene and graded alcohol series, as in routine processing. The endogenous peroxidase activity was blocked by hydrogen peroxidase treatment. Tissue samples were then washed with distilled water and transferred to Tris-buffered saline plus 0.5% TWEEN© 20, pH 7.4 (TBS-T) containing 5% normal goat serum for 30 minutes. Then, tissue samples were incubated with tyrosine hydroxylase (TH), type 1 dopamine receptor (D1R), type 1 muscarinic receptor (M1R), alpha-7 nicotinic receptor ($\alpha$-7R), $\alpha$-synuclein, phosphorylated tau (pTau) S396, phosphorylated 43-kDa TAR DNA-binding protein (pTDP43), sirtuin 1 (SIRT1), peroxisome proliferator-activated receptor (PPAR)-$\gamma$ coactivator-1 (PGC1), uncoupling protein 4 (UCP4) and MITOTRACKER™ at room temperature for 2 hours. Tissue samples were incubated with the secondary antibody (ALEXAFLUOR® 488, ALEXAFLUOR® 633, anti-mouse or anti-rabbit antibody) at room temperature for 1 hour. All antibodies were diluted in 2% non-immune goat serum in phosphate-buffered saline with TWEEN© (PBST) buffer. Tissue samples were incubated with 3,30-diaminobenzidine (DAB) for 5-10 minutes, and hematoxylin or 4′,6-diamidino-2-phenylindole (DAPI) was used for nuclear staining.

Statistical Analysis

Data were given as mean±standard error of the mean (mean±SE). Comparisons of the data between groups were calculated using Mann-Whitney's rank sum test and Wilcoxon's sum of rank test. $P<0.05$ was considered statistically significant.

Example 1 Effect of ATG-125 Solution on PD-Associated Proteins

As described in Materials and Methods, MPTP was used to induce the symptoms of PD in mice. The MPTP-induced mice were independently treated with specified treatments, including olive oil, ATG-125 solution, and selegiline, for 14 days. The expression levels of different PD-associated proteins, including TH, D1R, M1R, $\alpha$-7R, pTau S396 and pTDP43, in the brains of mice were examined in this example. The results were respectively depicted in FIGS. 1 to 4.

Figure 2:
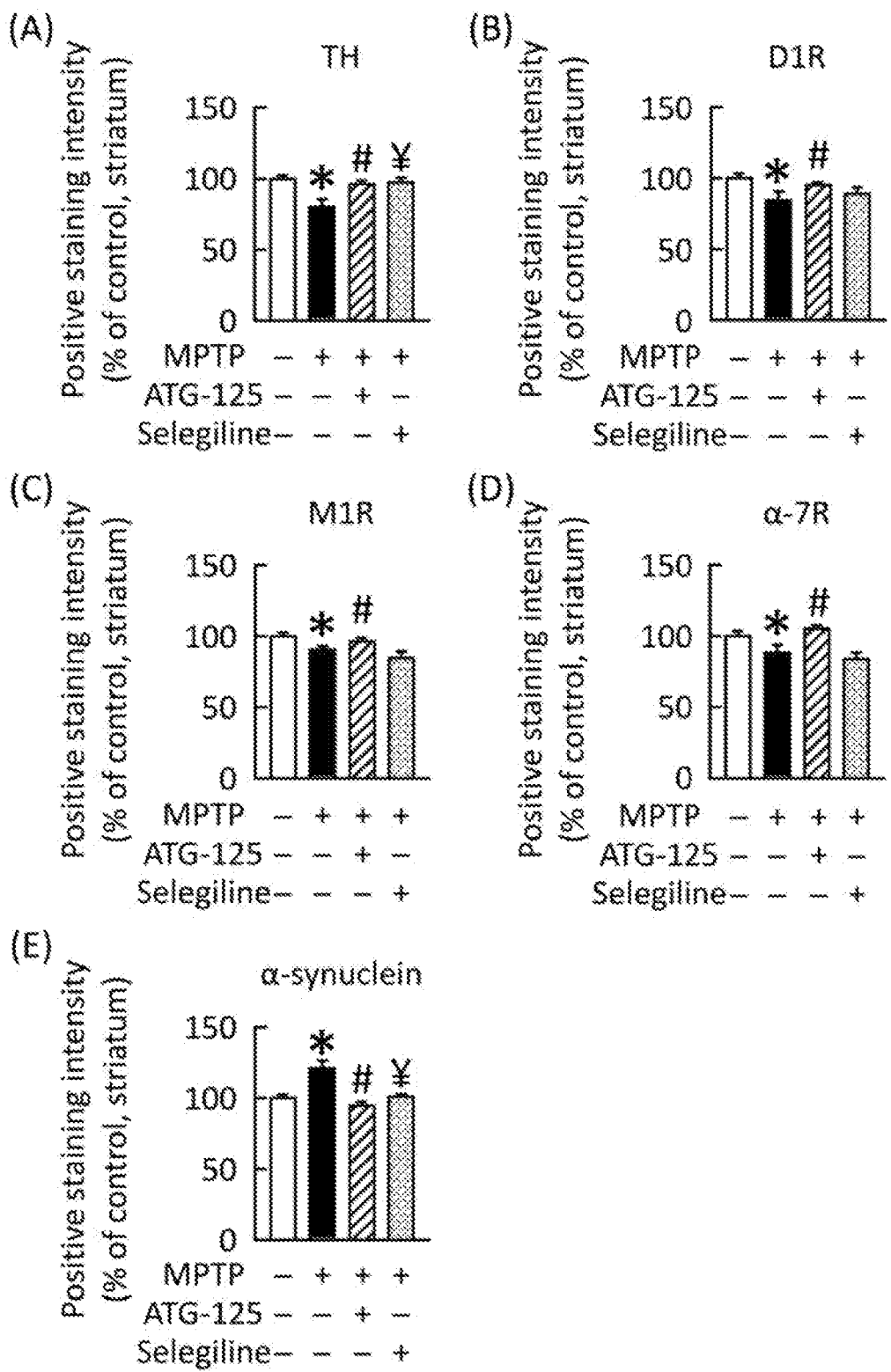
FIG. 2 depicts the effect of the present ATG-125 on the expression levels of TH (Panel (A)), D1R (Panel (B)), MIR (Panel (C)), α-7R (Panel (D)), and α-synuclein (Panel (E)) in the striatum of mice administered with specified treatments according to Example 1 of the present disclosure; for each animal group, n=5; *P<0.05, the normal control group compared to the MPTP group; #P<0.05, the MPTP group compared to the MPTP+ATG-125 group; YP<0.05, the MPTP group compared to the MPTP+selegiline group.
Figure 3:
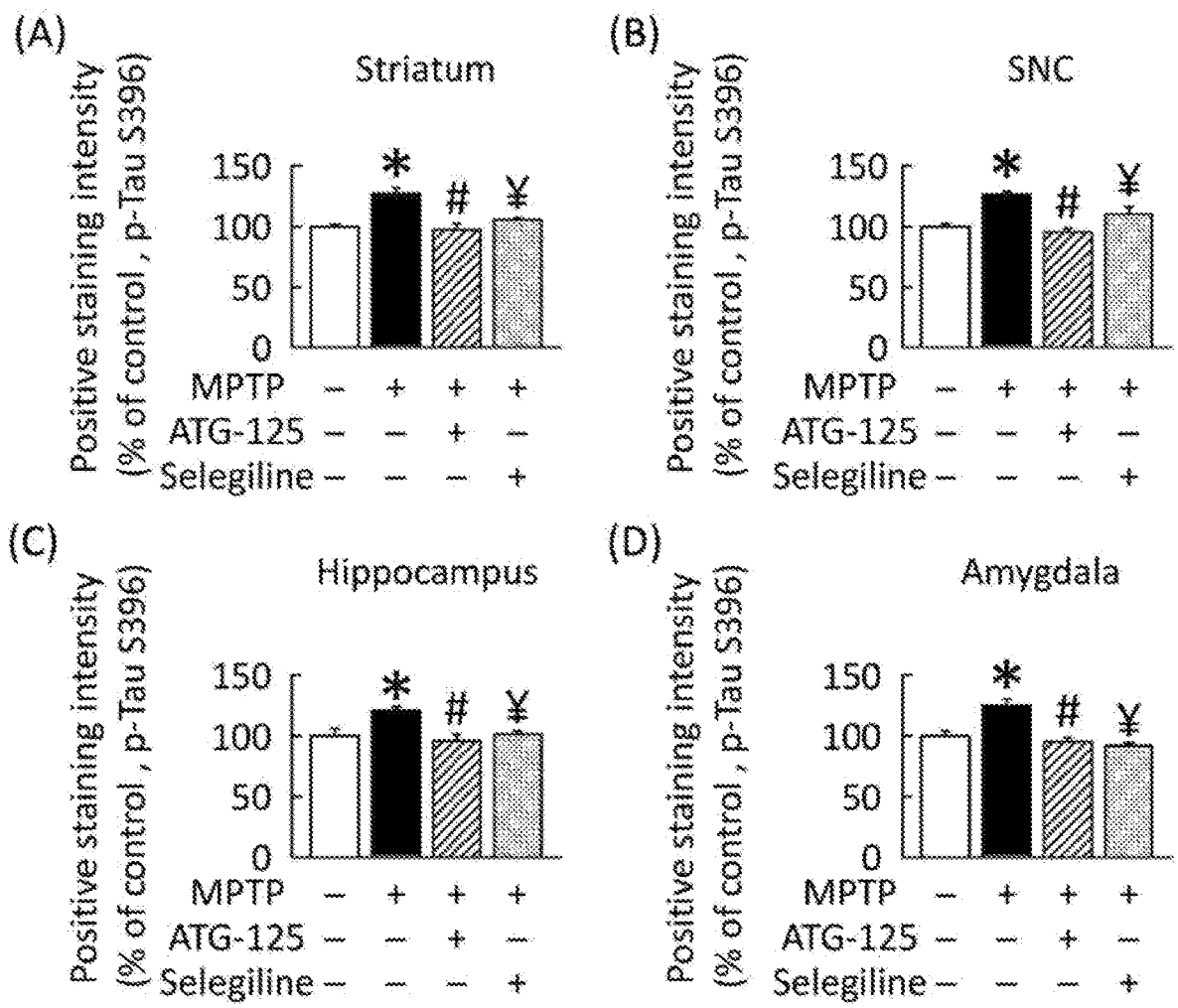
FIG. 3 depicts the effect of the present ATG-125 on the expression level of phosphorylated tau (pTau) S396 in the striatum (Panel (A)), SNC (Panel (B)), hippocampus (Panel (C)), and amygdala (Panel (D)) of mice administered with specified treatments according to Example 1 of the present disclosure; for each animal group, n=5; *p<0.05, the normal control group as compared to the MPTP group; #p<0.05, the MPTP group as compared to the MPTP+ATG-125 group; Vp<0.05, the MPTP group compared to the MPTP+selegiline group.
Figure 4:
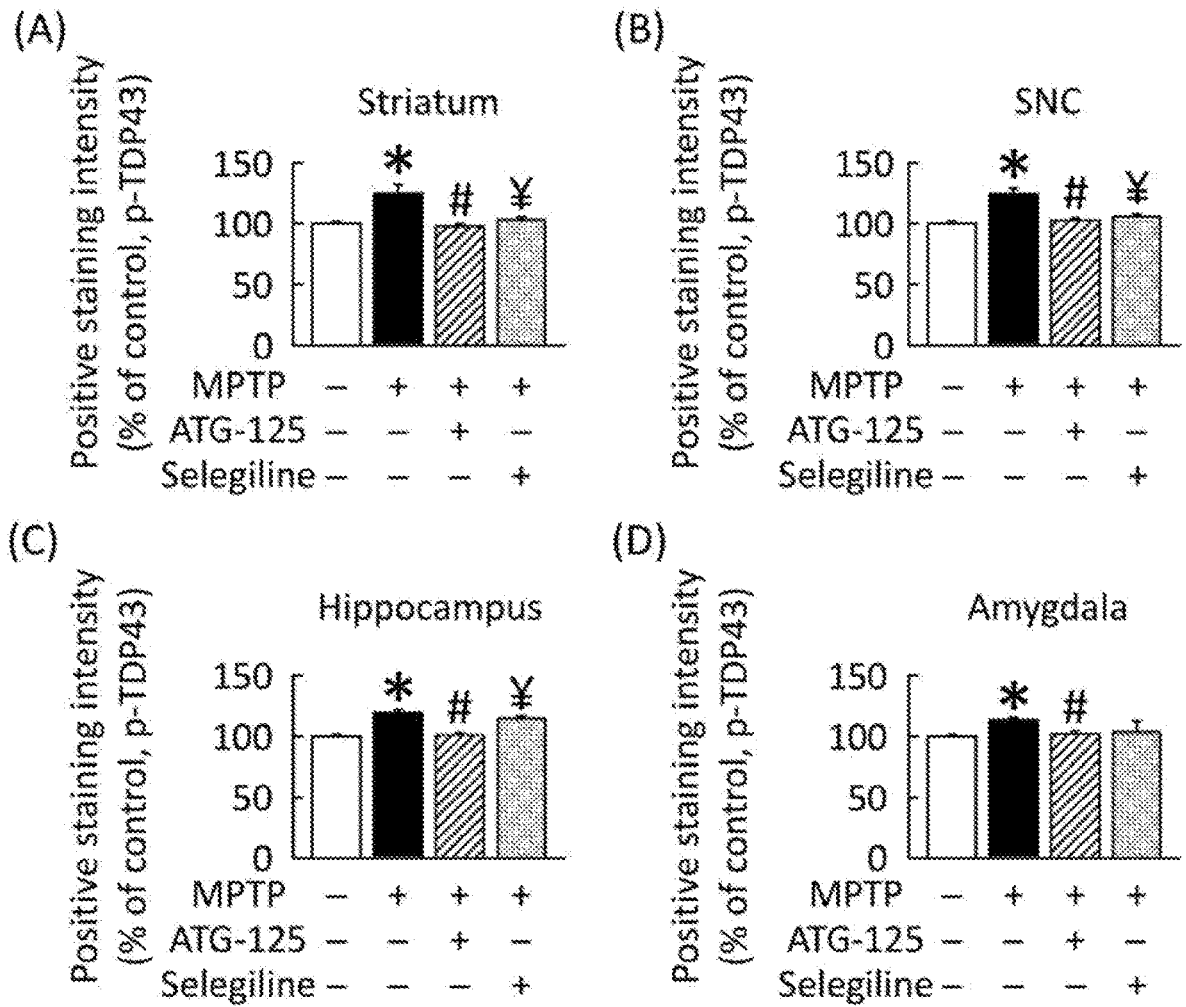
FIG. 4 depicts the effect of the present ATG-125 on the expression level of phosphorylated 43-kDa TAR DNA-binding protein (pTDP43) in the striatum (Panel (A)), SNC (Panel (B)), hippocampus (Panel (C)), and amygdala (Panel (D)) of mice administered with specified treatments according to Example 1 of the present disclosure; for each animal group, n=5; *p<0.05, the normal control group as compared to the MPTP group; #p<0.05, the MPTP group as compared to the MPTP+ATG-125 group; Yp<0.05, the MPTP group compared to the MPTP+selegiline group.

The data of FIGS. 1 and 2 indicated that MPTP down-regulated the expressed levels of TH, D1R, M1R, and $\alpha$-7R (four target proteins for treating PD; Panels (A) to (D) of FIGS. 1 and 2), while up-regulated the expressed level of $\alpha$-synuclein (a protein known to contribute to PD; Panel (E) of FIG. 1, and FIG. 2) in both substantia nigra (SNC; FIG. 1) and striatum (FIG. 2) of mice as compared to those in the normal control group. ATG-125 treatment significantly reversed the adverse effect of MPTP on brains (Panels (A) to (E) of FIGS. 1 and 2). It is noted that compared to selegiline, ATG-125 treatment provided a more beneficial effect on MPTP-induced mice (Panels (A) to (E) of FIGS. 1 and 2).

pTau and pTDP43 are two proteins involving in the development and progression of PD that aggregate and cause neuropathy in the brain. It was found that MPTP increased the levels of pTau S396 and pTDP43 in striatum (Panel (A) of FIGS. 3 and 4), SNC (Panel (B) of FIGS. 3 and 4), hippocampus (Panel (C) of FIGS. 3 and 4), and amygdala (Panel (D) of FIGS. 3 and 4). The treatment of ATG-125 solution significantly decreased the expression levels of these neurotoxic proteins in MPTP-induced mice (Panels (A) to (D) of FIGS. 3 and 4).

These results demonstrated that the present ATG-125 solution may provide a therapeutic effect on PD via regulating the expression of proteins in PD pathogenic pathway.

Example 2 Effect of ATG-125 Solution on Improving Mitochondrial Function

The dysfunction of mitochondria has been recognized as a key component in the progression of PD. Thus, whether ATG-125 solution would improve the mitochondrial function in PD animals was evaluated in this example, and the results were respectively depicted in FIGS. 5 to 7.

Figure 5:
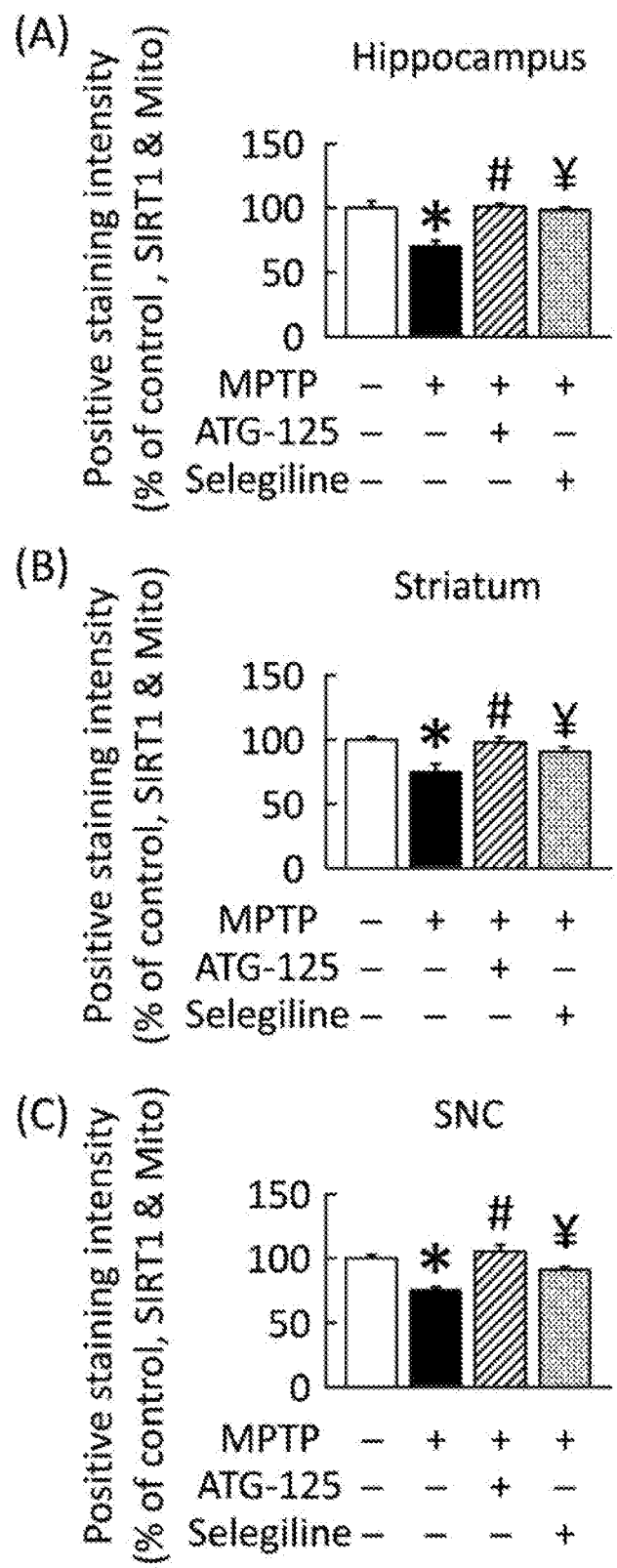
FIG. 5 depicts the effect of the present ATG-125 on the expression level of sirtuin 1 (SIRT1) in the hippocampus (Panel (A)), striatum (Panel (B)), and SNC (Panel (C)) of mice administered with specified treatments according to Example 2 of the present disclosure; for each animal group, n=5; *p<0.05, the normal control group as compared to the MPTP group; #p<0.05, the MPTP group as compared to the MPTP+ATG-125 group; Yp<0.05, the MPTP group compared to the MPTP+selegiline group.
Figure 6:
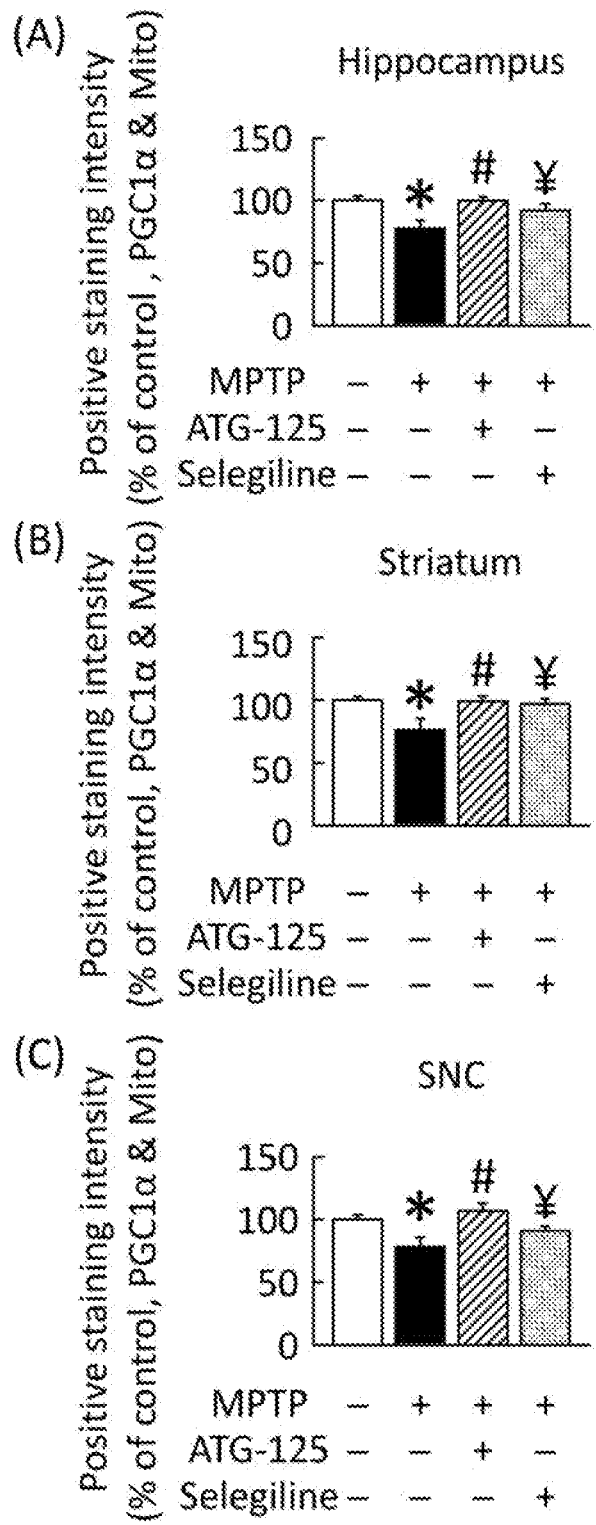
FIG. 6 depicts the effect of the present ATG-125 on the expression level of peroxisome proliferator-activated receptor (PPAR)-γ coactivator-1 (PGC1) in the hippocampus (Panel (A)), striatum (Panel (B)), and SNC (Panel (C)) of mice administered with specified treatments according to Example 2 of the present disclosure; for each animal group, n=5; *p<0.05, the normal control group as compared to the MPTP group; #p<0.05, the MPTP group as compared to the MPTP+ATG-125 group; Yp<0.05, the MPTP group compared to the MPTP+selegiline group.
Figure 7:
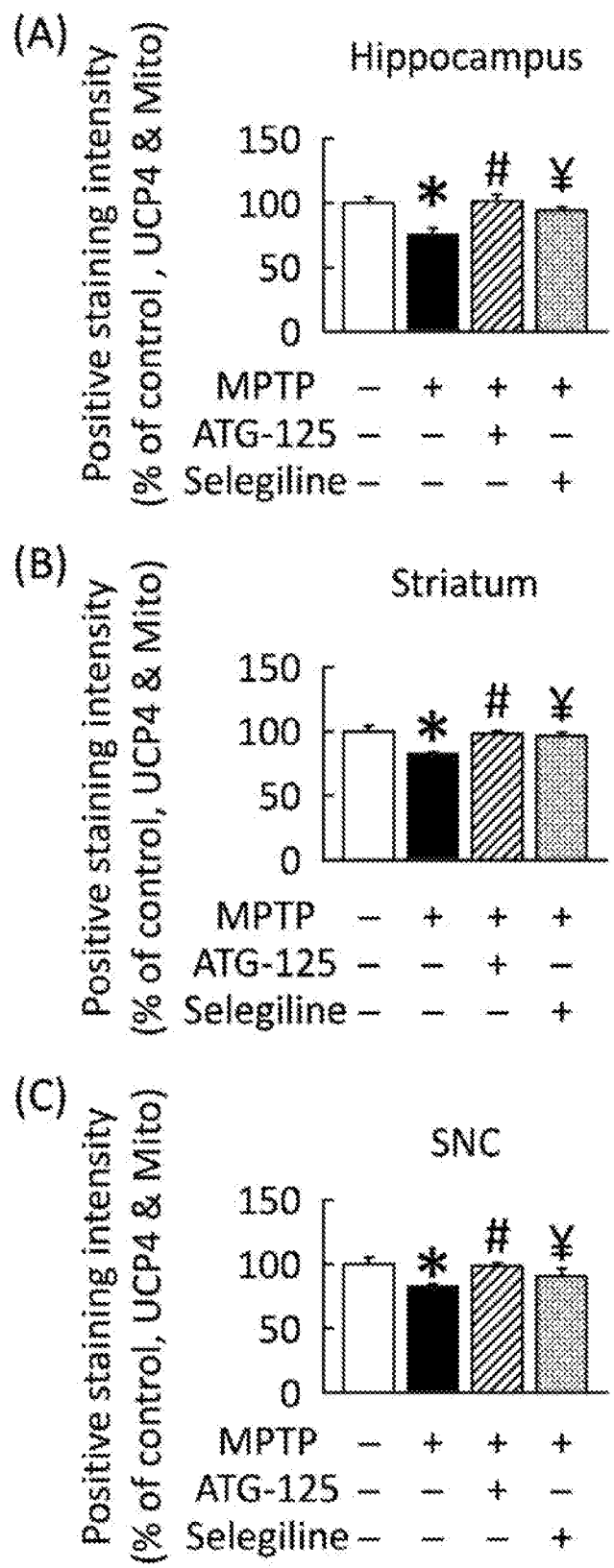
FIG. 7 depicts the effect of the present ATG-125 on the expression level of uncoupling protein 4 (UCP4) in the hippocampus (Panel (A)), striatum (Panel (B)), and SNC (Panel (C)) of mice administered with specified treatments according to Example 2 of the present disclosure; for each animal group, n=5; *p<0.05, the normal control group as compared to the MPTP group; #p<0.05, the MPTP group as compared to the MPTP+ATG-125 group; Yp<0.05, the MPTP group compared to the MPTP+selegiline group.

MPTP administration down-regulated the expression levels of SIRT1, PGCla, and UCP4 (three proteins known to mediate mitochondrial biogenesis and/or function) in both hippocampus (Panel (A) of FIGS. 5 to 7), striatum (Panel (B) of FIGS. 5 to 7), and SNC (Panel (C) of FIGS. 5 to 7) as compared to the normal control group, whereas ATG-125 treatment significantly restored the expression levels of these mitochondrial proteins in MPTP-induced mice. According to the results of FIGS. 5 to 7, ATG-125 exhibited a more beneficial effect than selegiline on MPTP-induced mice.

These data indicated that the present ATG-125 solution improved mitochondrial function in MPTP-induced mice.

In conclusion, the present disclosure provides a pharmaceutical composition (i.e., ATG-125 solution), which provides a potential means to treat PD via regulating protein expressions in PD pathogenic pathway and enhancing mitochondrial function in PD animals. Thus, the present pharmaceutical composition may serve as a therapeutic agent for preventing and/or treating PD thereby improving the life span and life quality of patients.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A pharmaceutical composition for treating Parkinson's disease, comprising,
    a mixture of chlorogenic acid, leonurine, schaftoside, rutin, isoschaftoside, isochlorogenic acid, 4,5-dicaffeoylquinic acid, quercetin, apigenin, glycyrrhizic acid, bisdemethoxycurcumin, demethoxycurcumin, curcumin, and artemisetin; and
    a pharmaceutically acceptable excipient.

2. The pharmaceutical composition of claim 1, wherein the mixture comprises 5-10 wt % of the chlorogenic acid, 0.1-2 wt % of the leonurine, 0.1-2 wt % of the schaftoside, 5-10 wt % of the rutin, 35-45 wt % of the isoschaftoside, 20-30 wt % of the isochlorogenic acid, 3-6 wt % of the 4,5-dicaffeoylquinic acid, 0.1-0.5 wt % of the quercetin, 1-3 wt % of the apigenin, 1-3 wt % of the glycyrrhizic acid, 1-3 wt % of the bisdemethoxycurcumin, 1-3 wt % of the demethoxycurcumin, 5-10 wt % of the curcumin, and 0.1-0.5 wt % of the artemisetin.

3. The pharmaceutical composition of claim 2, wherein the mixture comprises 7-8 wt % of the chlorogenic acid, 0.5-1 wt % of the leonurine, 0.5-1.5 wt % of the schaftoside, 7-8 wt % of the rutin, 38-42 wt % of the isoschaftoside, 20-25 wt % of the isochlorogenic acid, 4-5 wt % of the 4,5-dicaffeoylquinic acid, 0.1-0.3 wt % of the quercetin, 1-2 wt % of the apigenin, 1-2 wt % of the glycyrrhizic acid, 2-3 wt % of the bisdemethoxycurcumin, 2-3 wt % of the demethoxycurcumin, 5-7 wt % of the curcumin, and 0.1-0.3 wt % of the artemisetin.

4. A method of treating Parkinson's disease in a subject, comprising administering to the subject an effective amount of the pharmaceutical composition of claim 1.

5. The method of claim 4, wherein the pharmaceutical composition is orally administered to the subject.

6. The method of claim 5, wherein the pharmaceutical composition is administered to the subject daily for at least 7 days.

7. The method of claim 6, wherein the pharmaceutical composition is administered to the subject daily for 14 days.

* * * * *